United States Patent
Hacker et al.

(10) Patent No.: US 9,689,845 B2
(45) Date of Patent: Jun. 27, 2017

(54) ANGLE BEAM ULTRASONIC PROBE FOR INTERNAL HEX SOCKET BOLTS

(71) Applicant: AREVA Inc.

(72) Inventors: Michael G. Hacker, Goode, VA (US); Michael W. Key, Lynchburg, VA (US)

(73) Assignee: AREVA Inc., Lynchburg, VA (US)

( * ) Notice: Subject to any disclaimer, the term of this patent is extended or adjusted under 35 U.S.C. 154(b) by 600 days.

(21) Appl. No.: 13/894,535

(22) Filed: May 15, 2013

(65) Prior Publication Data

US 2013/0305826 A1 Nov. 21, 2013

Related U.S. Application Data

(60) Provisional application No. 61/648,681, filed on May 18, 2012.

(51) Int. Cl.

| G01N 29/00 | (2006.01) |
|---|---|
| G01N 29/28 | (2006.01) |
| G01D 11/30 | (2006.01) |
| G01N 29/07 | (2006.01) |
| G01N 29/22 | (2006.01) |

(52) U.S. Cl.
CPC ............ *G01N 29/28* (2013.01); *G01D 11/30* (2013.01); *G01N 29/07* (2013.01); *G01N 29/223* (2013.01); *G01N 2291/2691* (2013.01)

(58) Field of Classification Search
CPC ...................................................... G01N 29/28
USPC ................................................ 73/632, 866.5
See application file for complete search history.

(56) References Cited

U.S. PATENT DOCUMENTS

| 3,977,236 A | 8/1976 | Raatz, Jr. et al. |
|---|---|---|
| 5,095,753 A | 3/1992 | Russ et al. |
| 5,156,050 A | 10/1992 | Schmid et al. |
| 5,205,176 A * | 4/1993 | Kibblewhite ......... B06B 1/0662 |
| | | 204/192.15 |
| 5,661,242 A | 8/1997 | Schreiner et al. |
| 5,708,208 A | 1/1998 | Bonitz |
| 5,760,307 A | 6/1998 | Latimer et al. |
| 5,970,798 A | 10/1999 | Gleman et al. |
| 6,009,759 A | 1/2000 | Kibblewhite et al. |
| 6,158,285 A | 12/2000 | Latimer et al. |
| 6,332,361 B1 | 12/2001 | Yamada et al. |
| 6,523,412 B1 | 2/2003 | McClelland et al. |
| 7,131,345 B2 | 11/2006 | Achtzehn et al. |
| 7,900,516 B2 | 3/2011 | Fukutomi et al. |
| 2010/0101326 A1* | 4/2010 | Iizuka et al. .................... 73/588 |
| 2010/0257942 A1* | 10/2010 | Straub et al. .............. 73/861.28 |

(Continued)

*Primary Examiner* — Robert Huber
*Assistant Examiner* — Tarun Sinha
(74) *Attorney, Agent, or Firm* — Davidson, Davidson & Kappel, LLC

(57) ABSTRACT

A tool for inspecting the integrity of fasteners in their environment of use and methods of performing such inspections are disclosed and claimed. The tool includes a probe that matches the internal socket by which the fastener is coupled to the workpiece. The probe contains ultrasonic transducers on flat portions corresponding to flat portions of the socket. The transducers induce angled ultrasonic beams into the fastener to detect flaws therein. The beams are angled so they can be directed to the areas of interest at the head to shank region of the fastener. The presence of a defect such as a crack is determined based on the reply/echoes of the imparted ultrasonic beams.

16 Claims, 16 Drawing Sheets

(56) References Cited

U.S. PATENT DOCUMENTS

2012/0035862 A1* 2/2012 Kollgaard et al. .............. 702/39
2012/0222485 A1* 9/2012 Stickel ............................ 73/632

* cited by examiner

ANGLE BEAM ULTRASONIC PROBE FOR INTERNAL HEX SOCKET BOLTS

CROSS-REFERENCE TO RELATED APPLICATIONS

This patent application claims the benefit of U.S. Provisional Patent Application No. 61/648,681 filed on May 18, 2012, which is incorporated herein by reference in its entirety.

BACKGROUND OF THE INVENTION

1. Field of the Invention

The present invention relates to inspecting the integrity of fasteners, and, more particularly, the present invention relates to a device fir and method of inspecting fasteners in their environment of use.

2. Description of the Related Art

A typical requirement for industrial facilities, regardless of the type of industry, is that the equipment must be inspected on a routine basis to ensure that the structural integrity of the equipment is within acceptable guidelines. While the frequency of such inspections may vary, the need to prevent failure or break-down of the equipment is a common requirement across industry. For exemplary purposes, the environment of a nuclear utility will be discussed herein.

Nuclear utilities have a need to verify the integrity of their aging components within nuclear reactors and other plant systems. In Pressurized Water Reactors (PWRs), one exemplary set of components required to be inspected for plant life extension and compliance with regulatory requirements are the baffle bolts that are part of the reactor internal assembly. Due to the bolt pre-loads, age, and radiation fluence through the bolts, these fasteners are susceptible to loosening and cracking. Moreover, due to radiation embrittlement of the bolt materials (irradiation-assisted stress corrosion cracking, or IASCC), once a crack begins, it can grow quickly due to the reduced toughness of the embrittled material. Other influences may subject equipment in other types of facilities to similar degradation.

Industrial facilities typically have reduced access to fasteners once the equipment and related components are placed in service. In the environment of a nuclear power plant, retaining bars and/or washers are welded to the top of fasteners to prevent them from falling out if they become loose or if the head portion becomes detached from the shaft. These safety precautions make fastener inspection much more difficult and complex. Without a qualified and reliable inspection of the fasteners in their use configuration, the safety components must be removed to physically access the fastener. Thus, the facility operators will replace these fasteners regardless of whether they actually need to be replaced. Replacement, of course, is a much more costly and time consuming undertaking.

Thus, there is a need for a reliable and capable inspection system and method for fasteners with limited access.

SUMMARY OF THE INVENTION

The present invention relates to a tool for inspecting the integrity of fasteners in their environment of use. Baffle bolts of a nuclear reactor head are specifically contemplated as fasteners to be inspected. The tool includes a probe that matches the internal socket by which the fastener is coupled to the workpiece. The probe contains ultrasonic (UT) transducers on flat portions corresponding to flat portions of the socket. The transducers induce angled ultrasonic beams into the fastener to detect flaws therein. The beams are angled so they can be directed to the areas of interest at the head to shank region of the fastener. The presence of a defect such as a crack is determined based on the reply/echoes of the imparted ultrasonic beams.

When coupled with a multichannel UT instrument and associated software, the beams are activated in specified sequences to inject and receive the ultrasonic energy on various transducer elements to provide coverage of the entire circumference of the bolt. Various ultrasonic techniques are contemplated for use, including dual "side-by-side," dual "opposite" transducer pairs, and single element "pulse-echo." The "side-by-side" technique fires on one element and receives on the adjacent element. This sequence is incremented by one element around the probe until each of the elements has been fired. The "opposite" technique fires on one element and receives on the opposite element. This sequence is incremented once for each set of element pairs. The "pulse-echo" technique fires and receives on the same element, one at a time in sequence until all elements have been fired. All of these sequences repeat until data acquisition stops. The data files are stoned for off-line analysis.

DESCRIPTION OF THE DRAWINGS

The present invention is described with reference to the accompanying drawings, in which like reference characters reference like elements, and wherein.

DETAILED DESCRIPTION OF THE INVENTION

The present invention provides a tool for and method of inspecting the integrity of fasteners in their environment of use. While the present invention can be used with any type of fastener, baffle bolts of a nuclear reactor head will be discussed herein for exemplary purposes. Baffle bolts number in the hundreds in the reactor vessel and hold baffle plates together. The baffle plates allow a cylindrical vessel interior to accommodate the fuel, which is in square bundles. They also provide a boundary between incoming cold reactor coolant and the heated reactor coolant flowing on the outside and inside of the cylinder.

Figure 1:
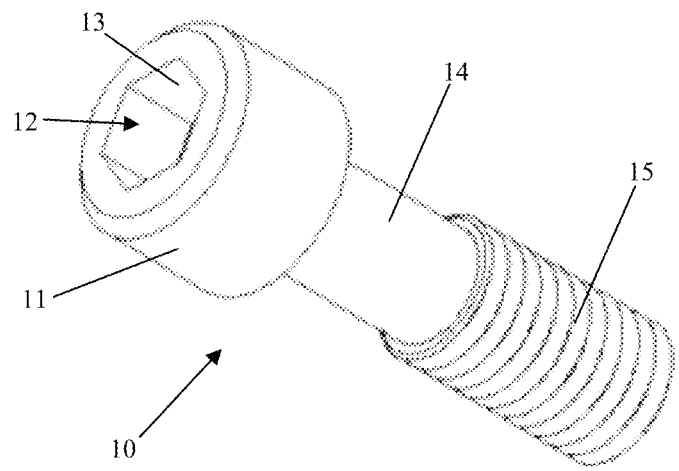
FIG. 1 shows a typical baffle bolt.

FIG. 1 shows a typical baffle bolt 10. The bolt 10 includes a head 11 and a shaft 14, which includes a threaded portion 15. The head 11 contains a socket 12 therein for engagement with a tool to engage or disengage the bolt 10. As shown in the illustrative example of FIG. 1, baffle bolts 10 typically have hexagonal sockets 12 having six flat sides or "flats" 13 by which the insertion/extraction tool provides torque to the bolt 10.

Typical ultrasonic inspection systems apply UT energy through the bottom of the sockets 12. The socket bottoms typically have a concave shape. However, the socket bottom typically is not controlled during the manufacturing process so the exact curvature is not known. Moreover, the manufacturing process by its nature, coupled with variations caused by machinery becoming worn and dulled during manufacture of the bolts 10, can cause a wide variation in the geometries of the socket bottoms. This is problematic for UT inspection, as the surface on which the transducer is placed must be well matched to the transducer contour in order to perform ultrasonic examinations. Thus, typical UT inspection systems are not able to provide accurate, reliable results for such widely varying socket bottom geometries.

Figure 2:
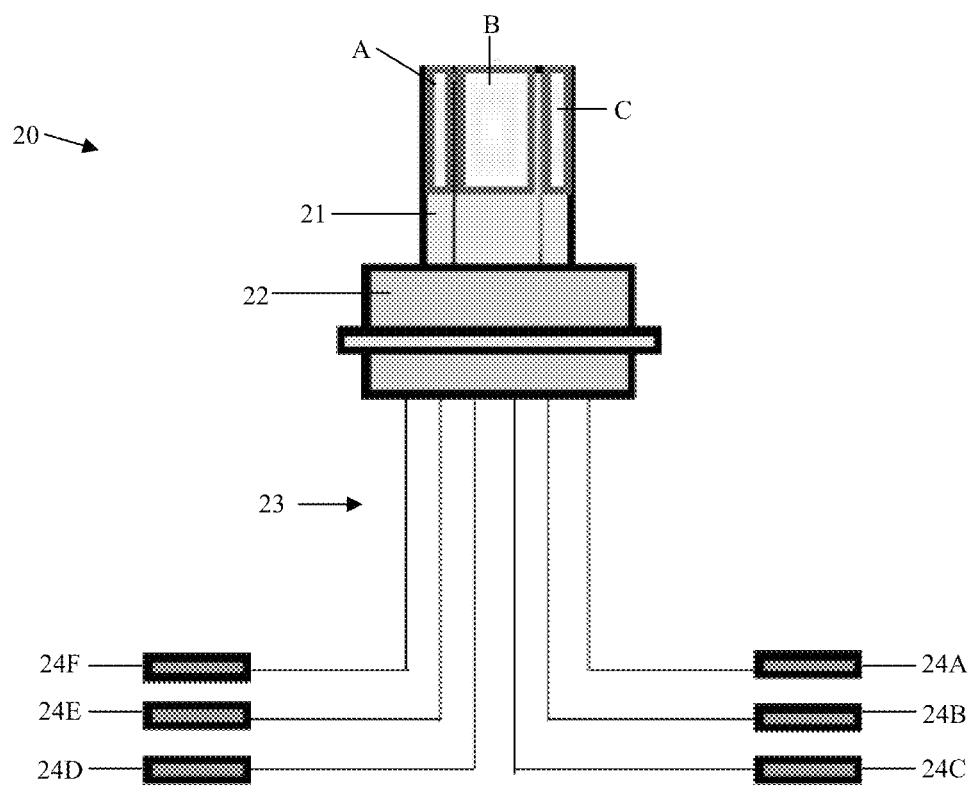
FIG. 2 shows a side view of a fastener inspection tool of the present invention.
Figure 3:
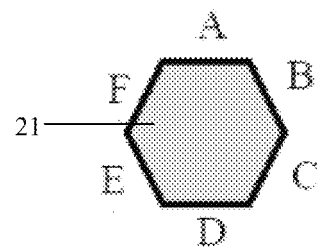
FIG. 3 shows a top view of the fastener inspection tool of FIG. 2.

The instant invention overcomes these measurement problems by applying UT energy to the bolt 10 through the socket flats 13. FIG. 2 shows a side view of a tool 20 of the present invention, and FIG. 3 shows a top view thereof. The tool 20 includes a probe head 21 coupled to a probe body 22. The probe head 21 is hexagonally shaped to match the socket 12 of the baffle bolts 10. Thus, the probe head 21 can access and inspect the baffle bolts 10 even when the top perimeter area of the bolt head 11 is inaccessible due to a retaining washer or the like.

The probe head 21 contains six transducers A-F, one transducer positioned on each of the sides corresponding to the socket flats 13. Wires 23 independently connect each transducer A-F to its corresponding controller 24A-24F. Thus, each transducer A-F can be independently controlled to impart or receive UT energy. The power supply, processing equipment, and other components are not shown.

The transducers A-F are configured to impart UT energy at a downward angle to the baffle bolt shaft 14. The imparted UT energy preferably is directed at an angle α of approximately 35°-55° relative to the longitudinal axis 16 of the bolt 10, with approximately 40°-45° being more preferred. The transducers A-F preferably are mounted in a housing that provides protection from damage and wear. The transducers A-F preferably are positioned so that the beam exit point is close to the tip of the probe head 21 to provide proper positioning of the sound beams when the probe 20 is seated in the bolt socket 12. Preferably, the transducers A-F are within approximately 0.12 in. from the tip of the probe head 21.

Figure 4:
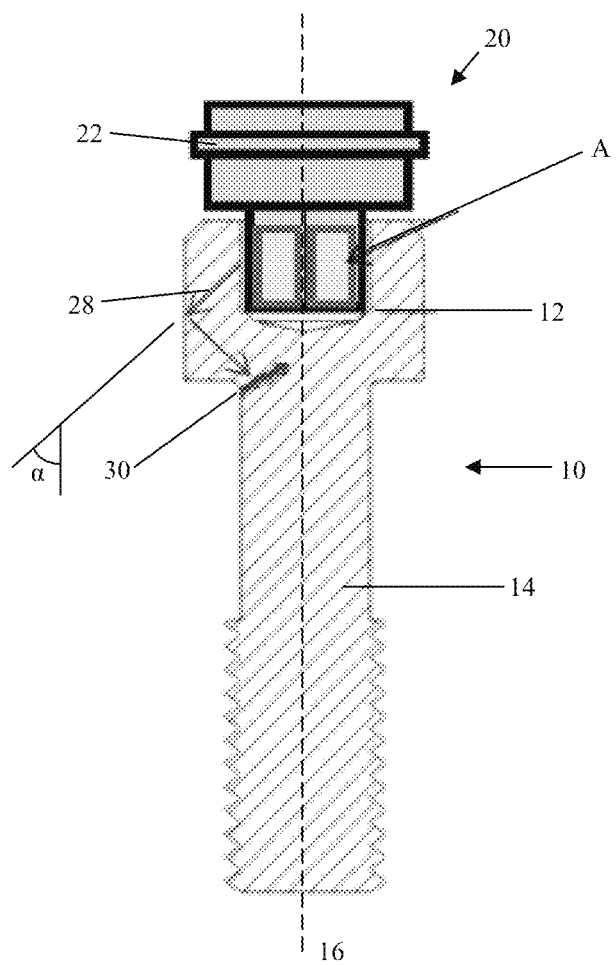
FIG. 4 shows the fastener inspection tool of FIG. 2 in its use position within the socket of the baffle bolt of FIG. 1.

FIG. 4 shows the probe 20 in its use position within the socket 12 of a baffle bolt 10. The socket 12 includes a number of flats 13 that are substantially parallel to the fastener longitudinal axis 16. As illustrated in the example embodiment of FIG. 4, the probe head 21 is configured to substantially fill the socket 12. In the event that the socket 12 is deeper and the probe head 21 does not extend to the bottom of the socket 12, it could be said that the probe head 21 substantially fills an elevation of the socket 12.

The probe head 21 includes a number flats corresponding to the number of socket flats 13 with a transducer positioned on each head flat such that when the probe head 21 is positioned within the fastener socket 12, a transducer is positioned adjacent each of the socket flats 13. Preferably, each transducer A-F spans 40%-60% of its respective socket flat 13. The transducers A-F are arranged in an array and are substantially evenly spaced adjacent the internal surface of the socket 12. Thus, the probe 20 can impart or receive UT waves 28 through any of the socket flats 13. The imparted sound beam 28 is reflected off of the outer diameter of the baffle bolt head 11 to the shaft 14 to detect any cracks 30 therein. This reflection is at the same angle as the incident angle imparted by the transducer. The beam 28 reflects off the crack and is sensed by the receiving transducer. A preferred nominal frequency for the beam 28 is approximately 4-6 MHz, and more preferably 5 MHz, which represents a compromise between high frequency for better resolution and lower frequency for less sensitivity to coupling interferences and better tolerance for flaw mis-orientation. Preferably, the transducer is a six channel transmitter/receiver.

When coupled with a multichannel UT instrument and associated software, the beams are activated in specified sequences to inject and receive the ultrasonic energy on various transducer elements to provide coverage of the entire circumference of the bolt. The ultrasonic techniques used with the probe 20 include dual "side-by-side" and dual "opposite" transducer pairs and single element "pulse-echo." The side-by-side technique fires on one element and receives on the adjacent element. This sequence is incremented by one element around the probe until each of the six elements has been fired. The opposite technique fires on one element and receives on the opposite element. This sequence is incremented once for each set of element pairs. The pulse-echo technique fires and receives on the same element, one at a time in sequence until all six elements have been fired. All of these sequences repeat until data acquisition stops. The data files are stored for off-line analysis. Table 1 below provides a summary of the ultrasonic techniques:

TABLE 1

| Acquisition Channel Naming Structure | | | |
| --- | --- | --- | --- |
| Transmit | Receive | Channel Name | Technique |
| A | B | AB | Dual Side-by-Side |
| B | C | BC | Dual Side-by-Side |
| C | D | CD | Dual Side-by-Side |
| D | E | DE | Dual Side-by-Side |
| E | F | EF | Dual Side-by-Side |
| F | A | FA | Dual Side-by-Side |
| A | D | AD | Dual Opposite |
| B | E | BE | Dual Opposite |
| C | F | CF | Dual Opposite |
| A | A | A | Pulse Echo |
| B | B | B | Pulse Echo |
| C | C | C | Pulse Echo |
| D | D | D | Pulse Echo |

TABLE 1-continued

Acquisition Channel Naming Structure

| Transmit | Receive | Channel Name | Technique |
|---|---|---|---|
| E | E | E | Pulse Echo |
| F | F | F | Pulse Echo |

Stress corrosion cracking typically consists of a sequence of facets and eventually branching in the bolt material. This structure creates scattering of the ultrasonic beam, which effect aids in flaw detection of tilted flaws using the dual side-by-side and pulse echo techniques described. In contrast, a smooth flaw is optimum for the dual-opposite technique. It should be noted, however, that a rough flaw would be expected to provide a lower signal to noise ratio response.

In a preferred method of operation, the software configures the UT instrument and acquires the data through the use of pre-established system setup files. These settings can be defined, for example, through experimentation on bolt sets containing flaws in order to optimize performance. After the data has been acquired, it may be stored on a hard drive attached to the data acquisition computer for archival purposes and for off-line analysis of the data. During the data acquisition process, the entire waveform may be digitally recorded for each channel with 12-bit resolution. Analysis of the data can also be performed with the software. Analysis of the data is performed by reviewing the displays for each of the data channels.

The probe 20 can be delivered to each bolt 10 to be examined using a variety of means. One preferred means is a remote controlled submarine. The delivery vehicle should have sufficient maneuverability to be able to deliver the probe 20 into the bolt socket 12. This may require that the probe 20 be rotated to align with the socket 12 and positioned relatively normal to the longitudinal axis of the bolt 10 to enable insertion. The delivery vehicle may preferably include a rail system and a transducer holder assembly that allows the transducer to traverse from side to side and to rotate the probe 20 about its axis to align with socket 12 of the bolt 10. Once the probe 20 is seated in the socket 12, the data acquisition sequence is started and the probe 20 is withdrawn from the socket 10. The data acquisition cycle may be timed such that the probe 20 has time to be withdrawn from the socket before recording stops. Tracking of the delivery vehicle may be accomplished using a map of the core barrel and auxiliary cameras to ensure the correct quadrant, plate, column, and former elevation are examined.

The basic principle for the examination of bolts 10 is the propagation of a sound field from the internal hex flat 13 through the side wall of the head to the outer diameter surface, and then back toward the center of the bolt 10 below the socket 12 in the head 11 to shank 14 region of the bolt 10. If there is a separation (crack) 30 in the material, which reflects part of the sound energy, the result is that signals will be detected by the techniques described herein and the bolt 10 will be identified as a cracked bolt 10. If a bolt 10 is determined to be cracked, it is considered non-functional and no further characterization is necessary.

A high signal-to-noise ratio (SNR) is optimal for flaw detection with minimal false calls. Because the grain structure is fine and the sound path to the flaws of interest is short, flaw response is expected to be good. It is expected that most bolts should provide on average a 3% to 5% noise level response.

Either shear wave or longitudinal wave angle beams modes can be used for the inventive application. However, the shear wave mode is preferred.

Figure 5:
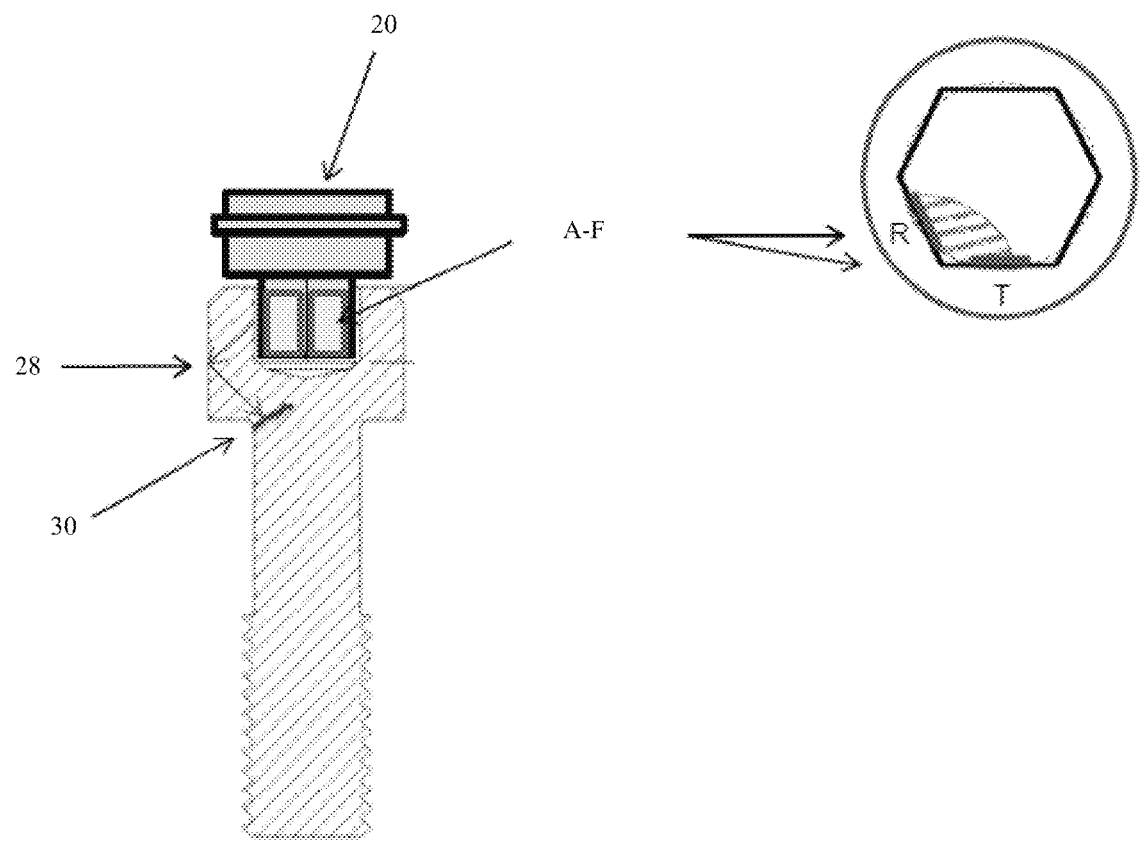
FIG. 5 shows an example dual side-by-side mode of operation of the inspection tool of FIG. 2.

The dual side-by-side technique uses each transducer A-F as a transmitter and the adjacent transducer as a receiver as shown in Table 1 to create six channels of data. This technique can be used to detect angled flaws in the head to shank region of the bolt 10. During the data acquisition cycle, the transmitter and receiver pairs are electronically incremented around the probe 10 to activate all transducer pairs sequentially. This technique is illustrated in FIG. 5, which shows a transmitting transducer T adjacent a receiving transducer R. The left side of FIG. 5 presents a cross-sectional view showing the beam 28 reflecting off of the outer diameter surface of the head 11 and traveling to an area of interest. If a flaw 30 is in the beam path and tilted at an angle with sufficient circumferential extent, it will reflect some of the energy back to the receiver on the adjacent flat 13 and be detected. The face of tilted flaws is expected to be somewhat spherical in shape because the crack will follow the circumference of the bolt 10 as it progresses upward and toward the center of the bolt 10. This shape helps direct the reflected energy toward the receiver R and aids in detection of the flaw 28. However, to be detected with this technique, the flaw circumferential position relative to the flats 13 must extend at least partially across two flats (approximately 60°) as shown in the left side of FIG. 5.

Figure 6:
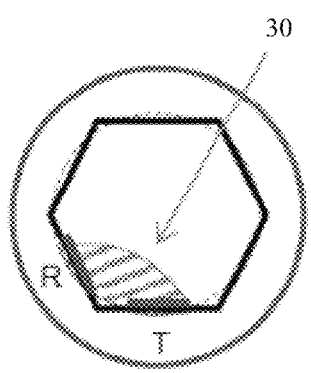
FIG. 6 shows an example flaw that is centered on the intersection of two bolt socket flats.
Figure 7:
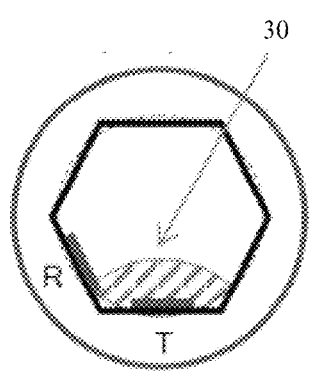
FIG. 7 shows an example flaw that is centered on only one bolt socket flat.
Figure 8:
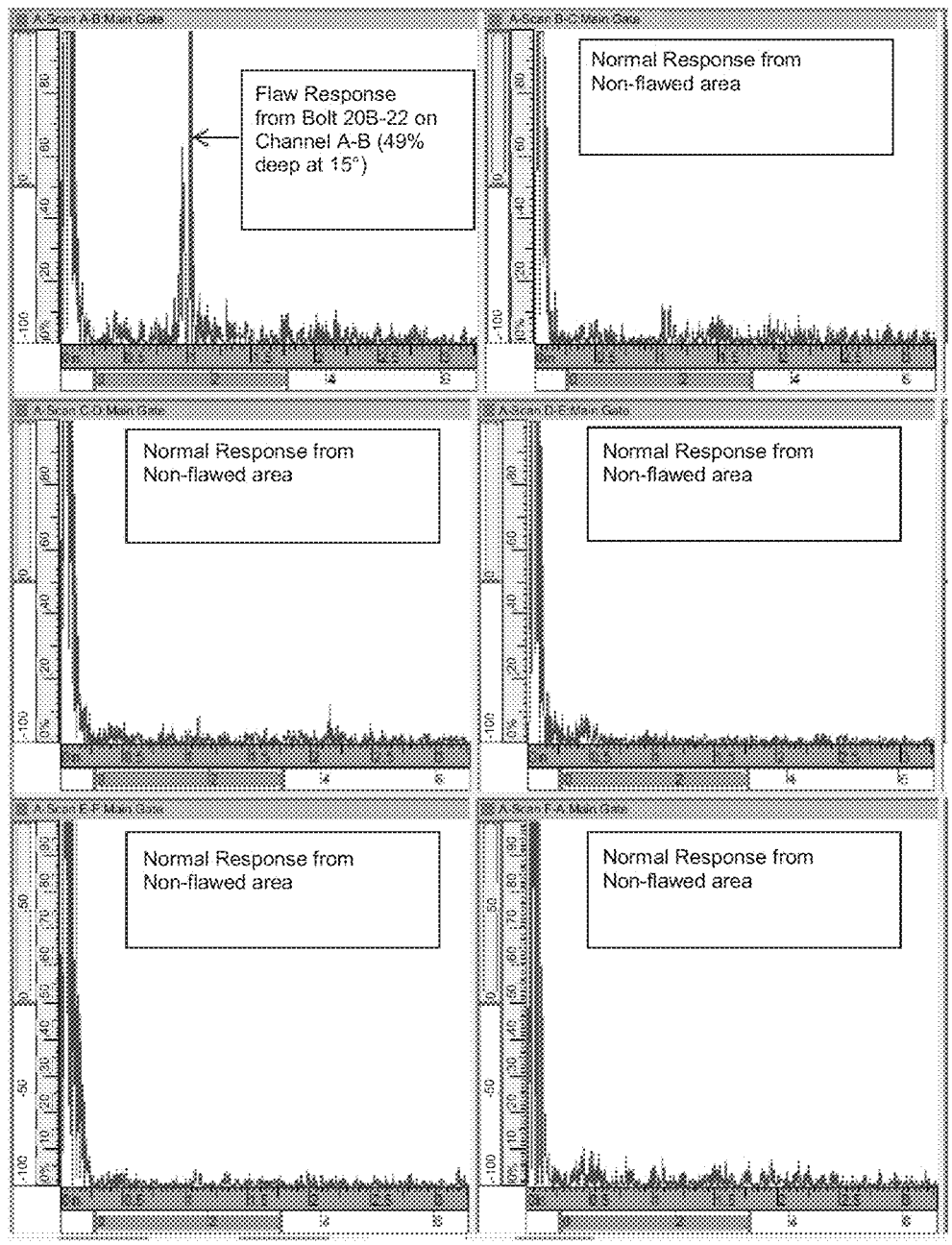
FIGS. 8-11 each show typical baffle bolt UT responses from flaws of varying tilt angles and flaw depths measured with the dual side-by-side technique of the present invention.
Figure 9:
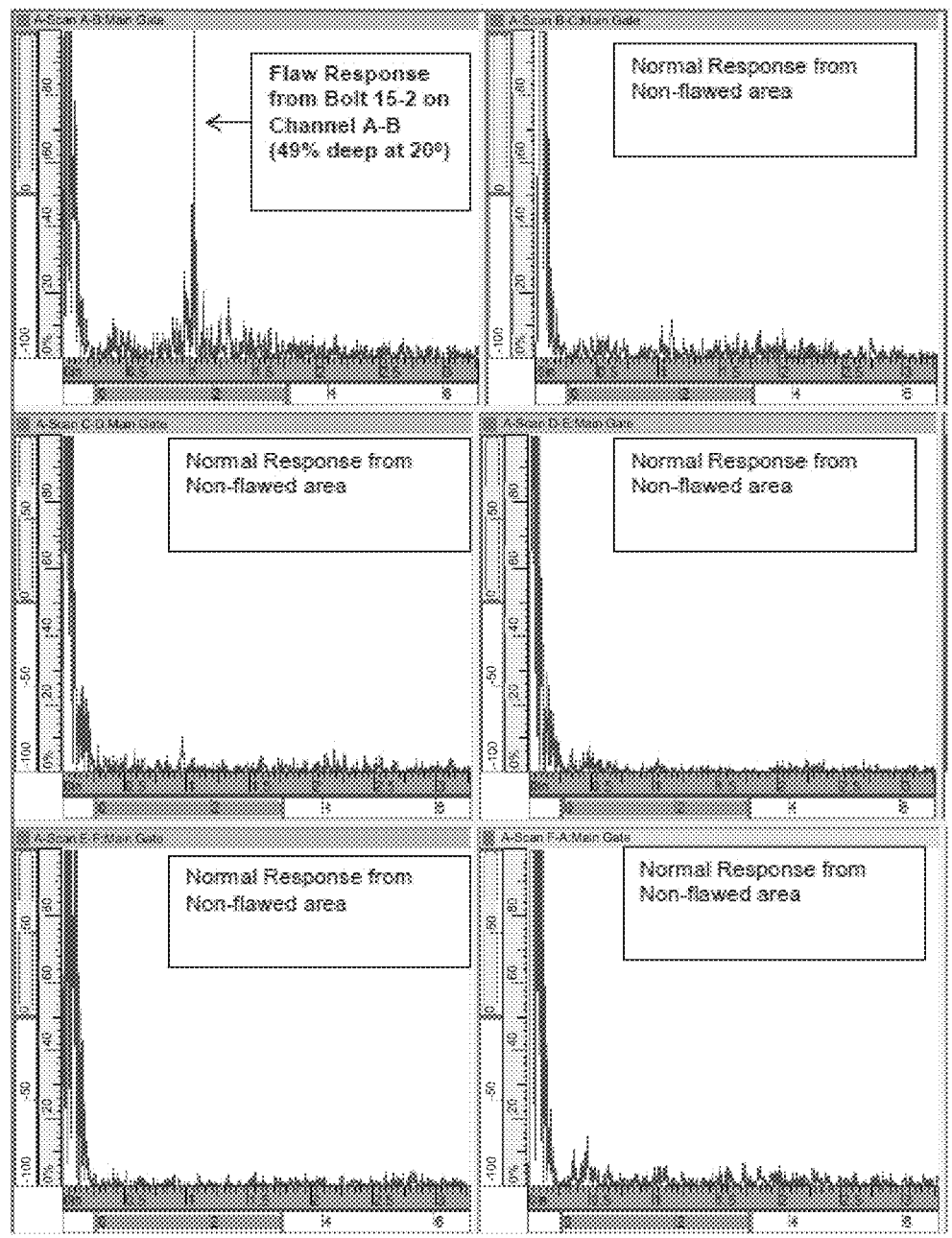
Figure 10:
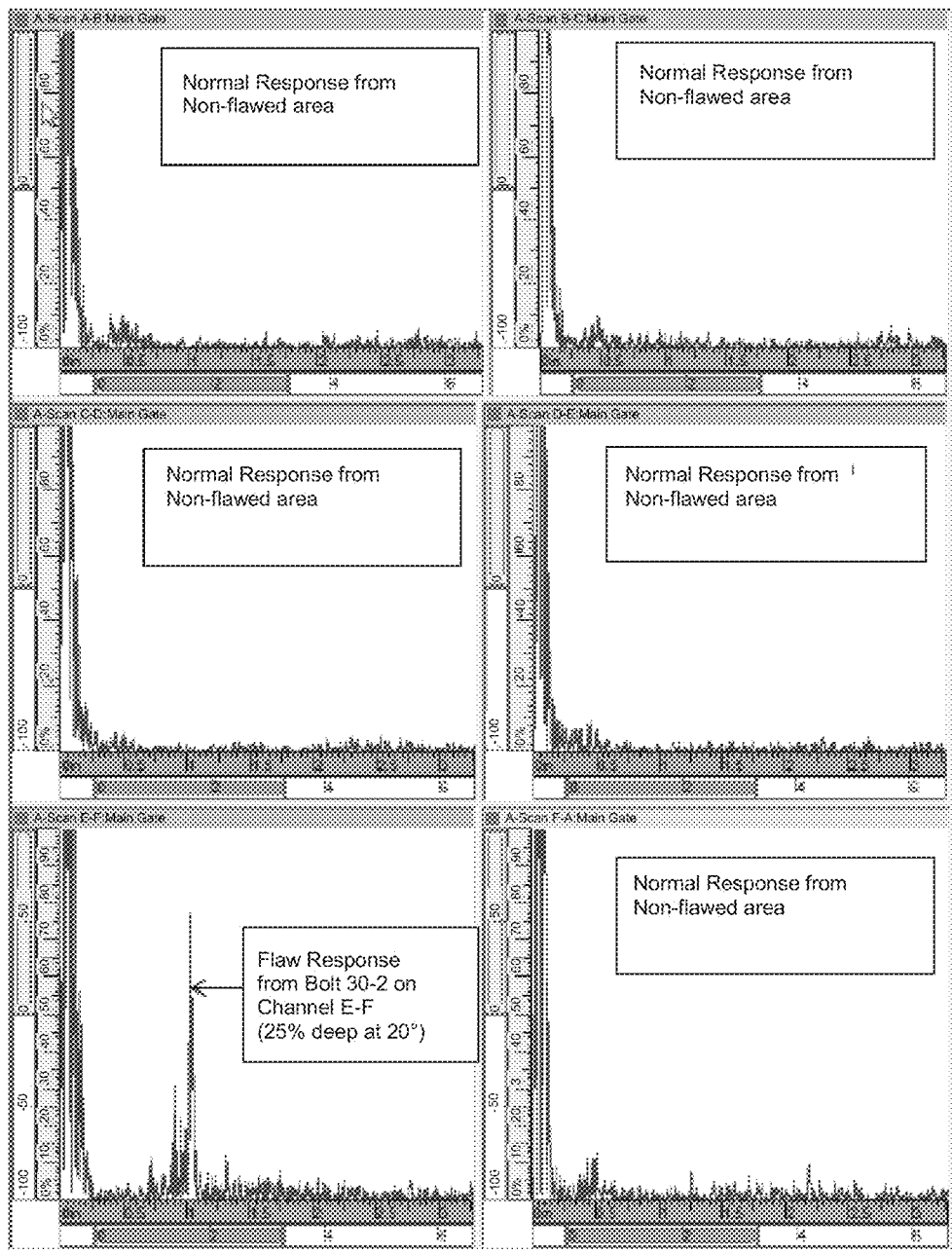
Figure 11:
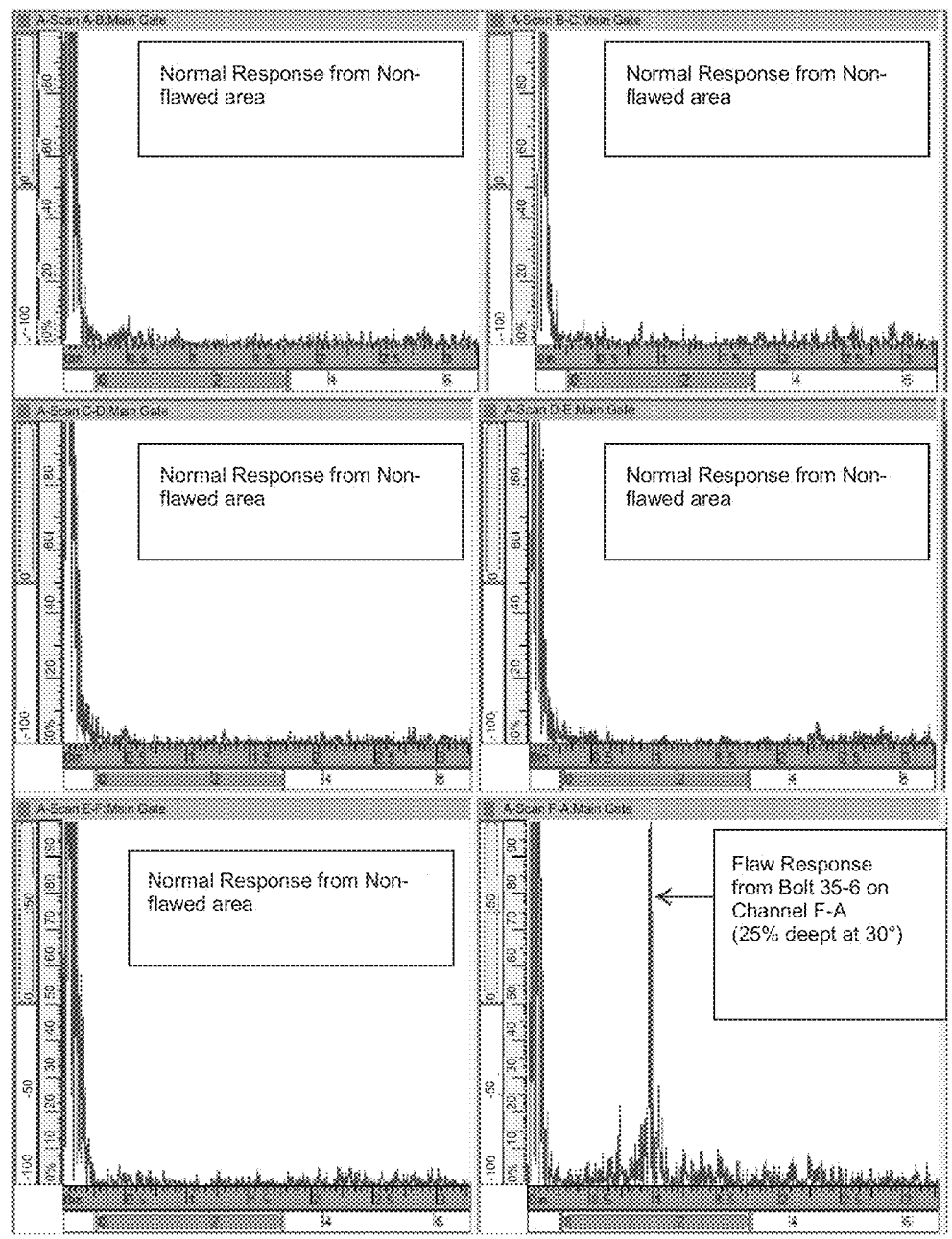

FIGS. 6 and 7 present top views from the bolt head 11 and show the effect of flaw 28 position relative the flats 13 for detection for the dual side-by-side technique. FIG. 6 illustrates an elliptically shaped flaw 28 that is centered on the intersection of two flats 13. The flaw 28 is approximately 25% deep. This is the optimum flaw position for this technique. FIG. 7 illustrates the same flaw as FIG. 6, but it is on only one of the flats 13. This is not an optimum flaw position for this technique because the reflected energy may not reach the receiver. Detection of these flaws 28 is addressed by the pulse-echo technique described below.

Deeper flaws are likely to span multiple flats 13 and be detected with multiple side-by-side channels. In this regard, the number of channels that detect a flaw may be an indicator of the flaw depth; however, flaw size is not relevant to disposition the condition of the bolt 10. The method used to minimize false calls with this technique involves a second acquisition of the data but with the probe rotated at least 60°. If the indication is relevant, it will move to the channel(s) corresponding to the probe rotation. For example, if the indication was detected on channels CD and DE during the first acquisition and then after rotating the probe 60° the indication appears on channels DE and EF, the indication will be considered relevant and the bolt considered cracked. If the indication does not change channels corresponding to the probe rotation position, it can be considered non-relevant.

FIGS. 8-11 each show typical baffle bolt UT responses from flaws of varying tilt angles and flaw depths measured with the dual side-by-side technique. Responses obtained from non-flawed areas of the bolt are also shown. The images include the displays from each of the six channels used for this technique. As evidenced by the responses, flaws ranging from 15° to 30° tilts are easily detectable with good signal to noise ratio.

The pulse-echo technique uses each of the six transducers A-F separately as transmitters/receivers in a pulse-echo mode. Table 1 lists each of the six channels. This technique can be used to supplement the dual side-by-side technique to detect angled flaws at the head to shank region of the bolt 10 that are restricted primarily to only one of the flats 13. This condition exists for shallow flaws where the circumferential extent is short. During the data acquisition cycle, the transducers A-F are electronically incremented around the probe 20 to activate all transducers sequentially. This technique is illustrated in FIG. 12.

Figure 12:
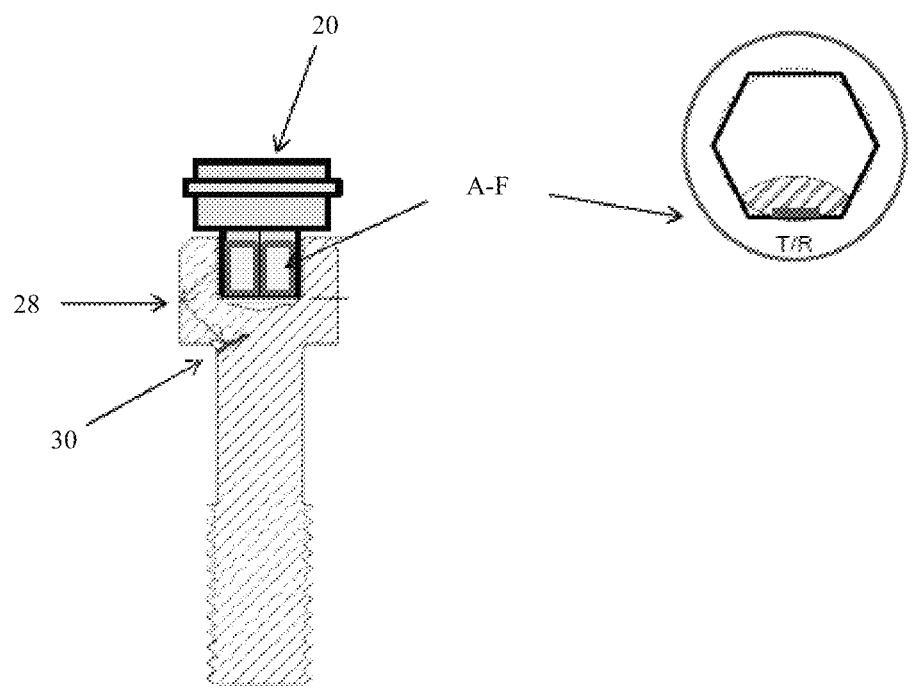
FIG. 12 shows an example pulse-echo mode of operation of the inspection tool of FIG. 2.

The left side of FIG. 12 presents a cross-sectional view showing the beans 28 reflecting off of the outer diameter surface of the head 10 and traveling to an area of interest. If a flaw 30 is in the beam path and tilted at an angle with sufficient circumferential extent, it will reflect some of the energy back to the transducer A-F and be detected. Because detection is based on the beam 28 traveling along the same path for the transmitted and reflected beams, this technique is the most sensitive to small flaws.

Figure 13:
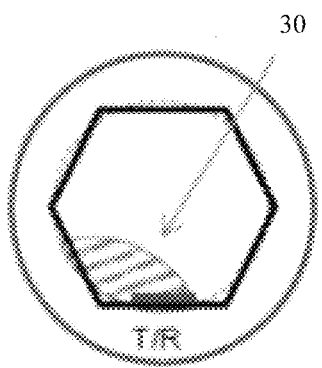
FIG. 13 shows an example flaw that is centered on the intersection of two bolt socket flats.
Figure 14:
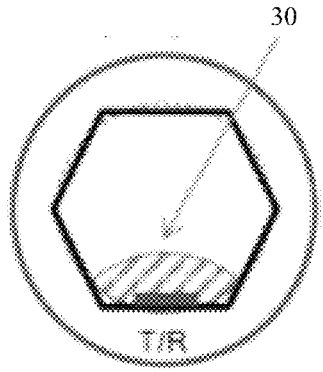
FIG. 14 shows an example flaw that is centered on only one bolt socket flat.

FIGS. 13 and 14 present top views from the bolt head 11 and shows the effect of flaw 30 position relative the flats 13 for detection with the pulse-echo technique. FIG. 13 illustrates an elliptically shaped flaw 30 that is approximately 25% deep and centered between two flats 13. This is the least optimum position for this technique because the sound beam 28 only interacts with a small fraction of the flaw surface area. Very shallow flaws with this orientation may escape detection with this technique because the reflected energy will likely not reach the receiver R. FIG. 14 illustrates the same flaw as FIG. 13, but it is on only one of the flats 13. Shallow flaws with this alignment will likely be detected because the reflecting surface of the flaw 30 will direct most of the energy back to the transducer.

Deeper flaws are likely to span multiple flats 13 and be detected with multiple pulse-echo channels. In this regard, the number of channels that detect a flaw may be all indicator of the flaw depth; however, flaw size is not relevant to disposition the bolt 10. The method used to minimize false calls with this technique involves a second acquisition of the data but with the probe rotated at least 60°. If the indication is relevant, it will move to the channels corresponding to the probe rotation. For example, if the indication was detected on channels C and D during the first acquisition and then after rotating the probe 60° the indication appears on channels D and E, the indication will be considered relevant and the bolt considered cracked. If the indication does not change channels corresponding to the probe rotation position, it can be considered non-relevant.

Figure 15:
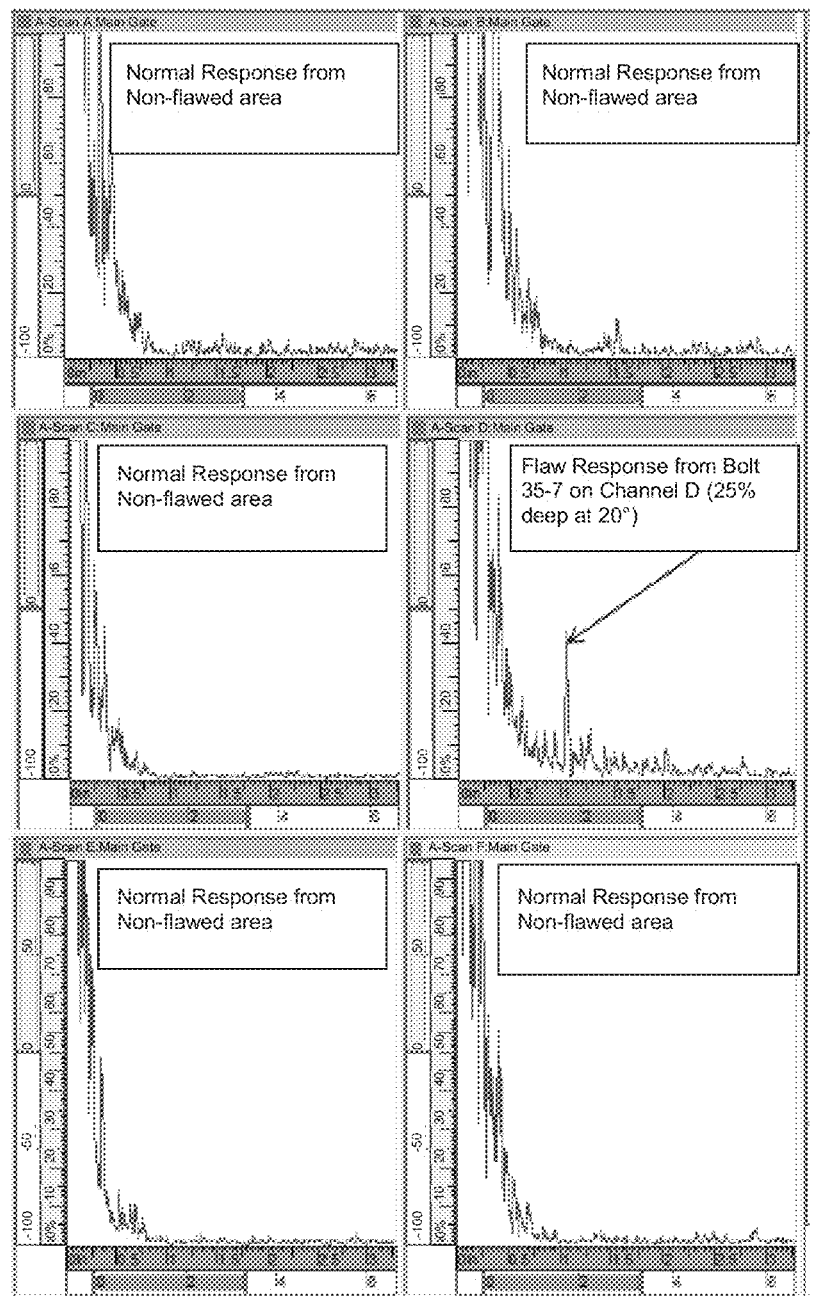
FIGS. 15-17 each show typical baffle bolt UT responses from flaws of varying tilt angles and flaw depths measured with the pulse-echo technique of the present invention.
Figure 16:
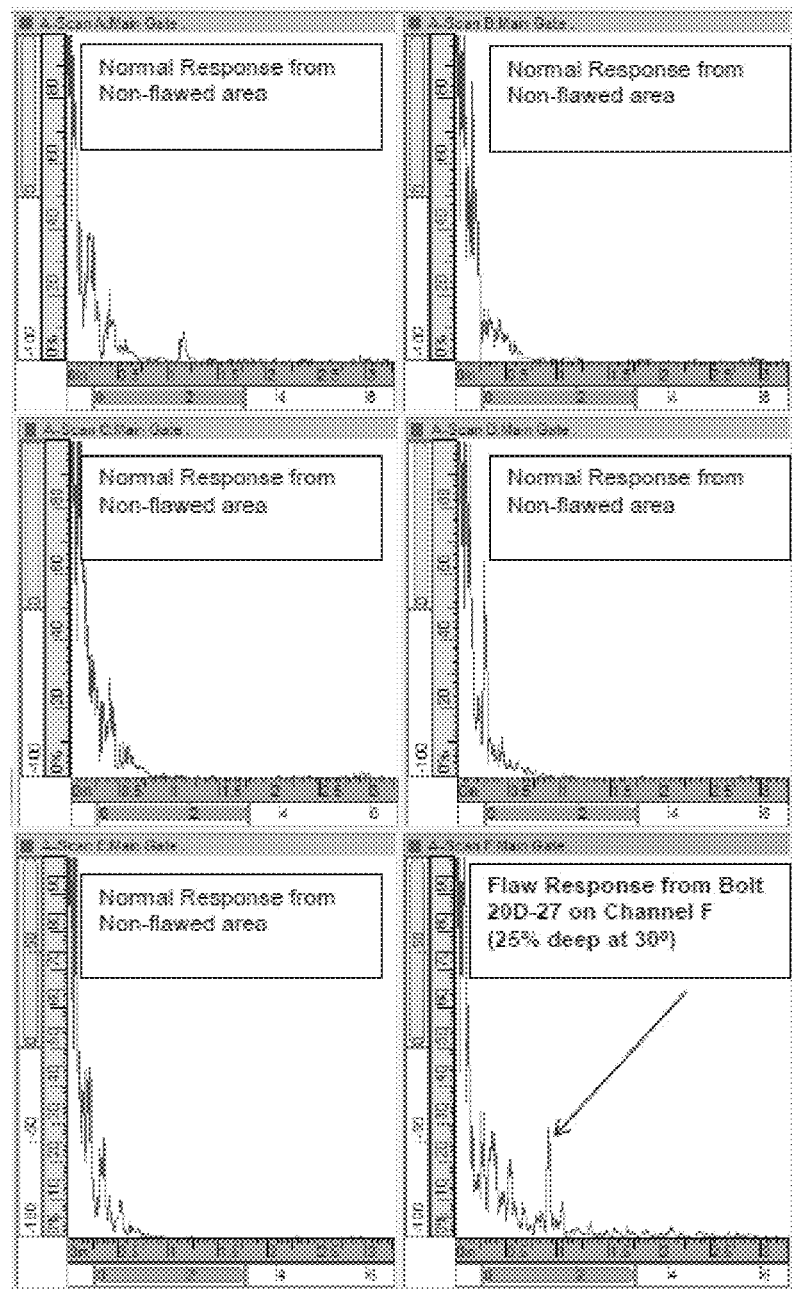
Figure 17:
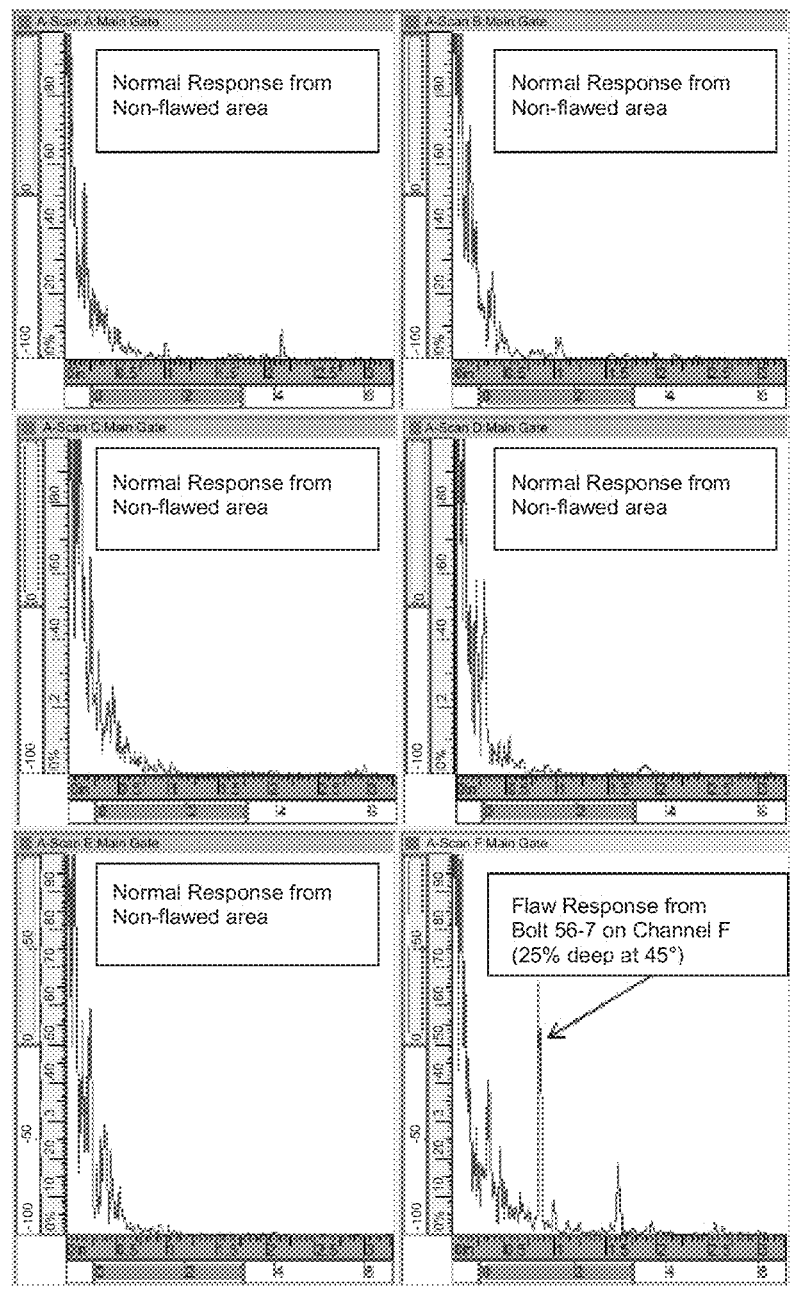

FIGS. 15-17 each show typical UT responses from flaws with various tilt angles and 25% flaw depths with the pulse-echo technique. The images include the displays from each of the six channels used for this technique. As evidenced by the responses, flaws are easily detectable with good signal to noise ratio.

The dual-opposite technique uses three of the transducers A-F as transmitters T and the three (opposed) transducers as receivers R configured in pairs as shown in Table 1 to create three channels of data. This technique can be used to detect flat flaws (little or no tilt angle) in the head to shank region of the bolt 10. During the data acquisition cycle, the transmitter T and receiver R pairs are electronically incremented around the probe to activate all transducer pairs sequentially. This technique is illustrated in FIG. 18.

Figure 18:
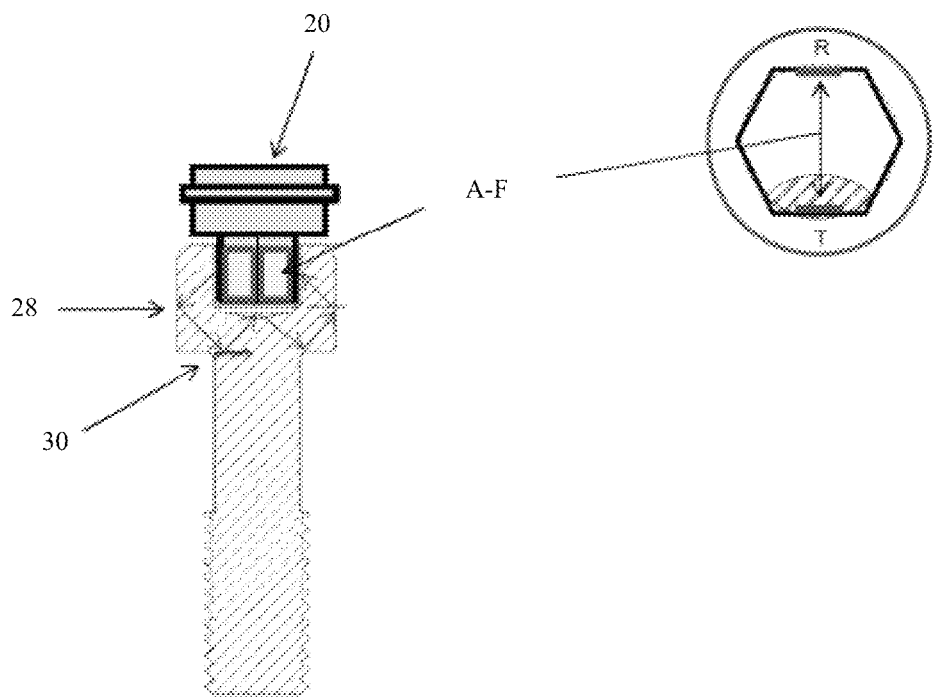
FIG. 18 shows an example dual-opposite mode of operation of the inspection tool of FIG. 2.

The left side of FIG. 18 presents a cross-sectional view showing the beam 28 reflecting off of the outer diameter surface of the head 10 and traveling to an area of interest. If a flaw 30 is in the beam path and relatively flat with sufficient radial extent, it will reflect the energy toward the bottom of the socket 12, reflect off the bottom of the socket 12 to the opposite shoulder, reflect to the bolt head outer diameter surface, and then to the receiving transducer R and be detected. In the absence of a flaw, some energy will reflect off of the shoulder and be directed toward the opposite side due to the width of the bolt shoulder. If the bottom of the socket 12 is conical, much of this energy will be scattered and little response will be detected on the opposite side of the bolt 10. However, if the bottom of the socket 12 is relatively flat, a greater portion of the energy will be reflected to the opposite side and will be detected. This amplitude response is expected to be relatively uniform in non-flawed bolts 10 for all three channels because the bolt head 11 and socket 12 geometry are symmetric. The presence of a flat flaw at the head to shank intersection will cause a change in the symmetry of the bolt head shoulder and cause a change in the amount of reflected energy that is transmitted to the receiver R. The effect will be an indication response that is greater than the amplitude observed on the non-affected channel(s). Depending on the actual flaw shape, detection may also be evident on the dual side-by-side or pulse-echo channels as well.

To determine if the response is due to a flaw or "flat" bottom socket geometry, the bolt socket 12 will need to be reviewed with video. If the bottom socket geometry is conical then it can be concluded that the response is due to a flaw. If the bottom so&et geometry is observed to be relatively flat and the amplitude of the indication is greater than that of an unflawed bolt with flat bottom geometry, then it can be concluded that the bolt is cracked. The depth of the flaw affects the amplitude of the flaw up until the flaw size exceeds the beam width because the increase in flaw size increases the reflecting surface resulting in more energy reaching the receiver. Depending on flaw roughness, the dual side-by-side or the pulse echo technique may also see the flaw at a lower amplitude response. If a flaw response is also present with the dual side-by-side or the pulse-echo techniques, then video confirmation of the socket geometry is not necessary.

Figure 19:
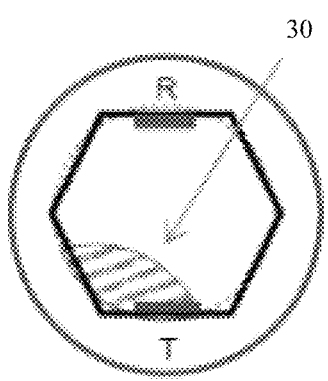
FIG. 19 shows an example flaw that is centered on the intersection of two bolt socket flats.
Figure 20:
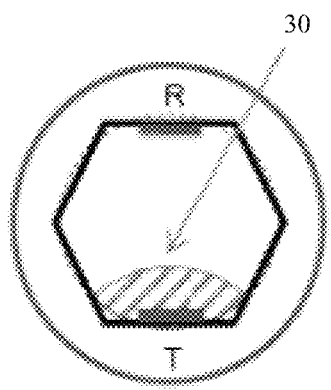
FIG. 20 shows an example flaw that is centered on only one bolt socket flat.
Figure 21:
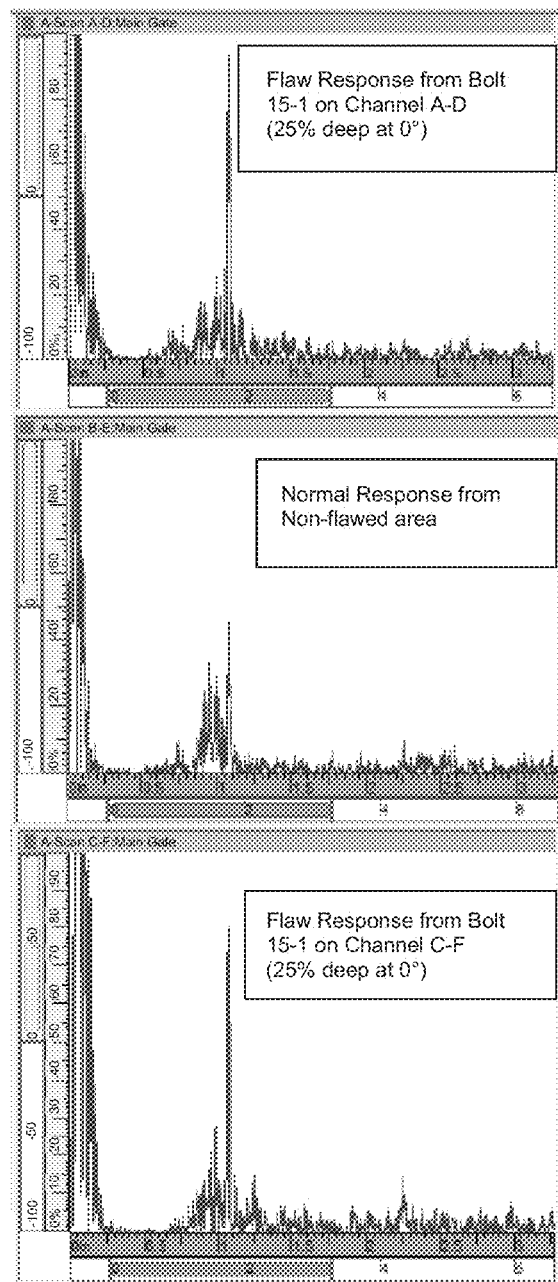
FIGS. 21-24 each show typical baffle bolt UT responses from flaws with no tilt angle and approximately 25% flaw depths measured with the dual-opposite technique of the present invention.
Figure 22:
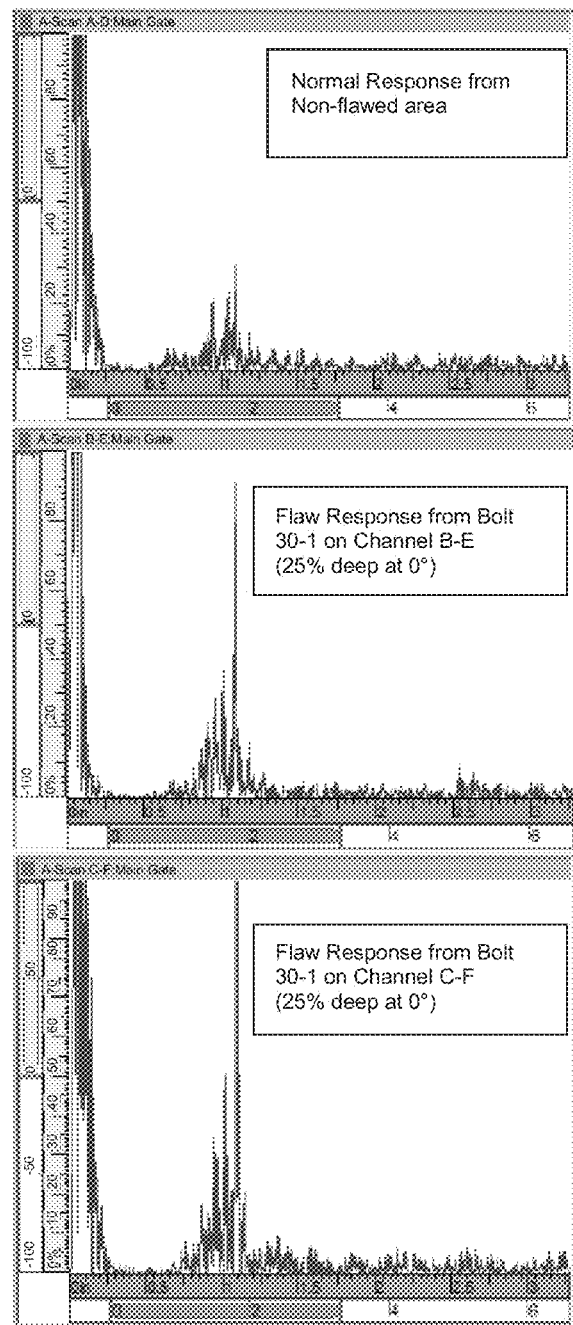
Figure 23:
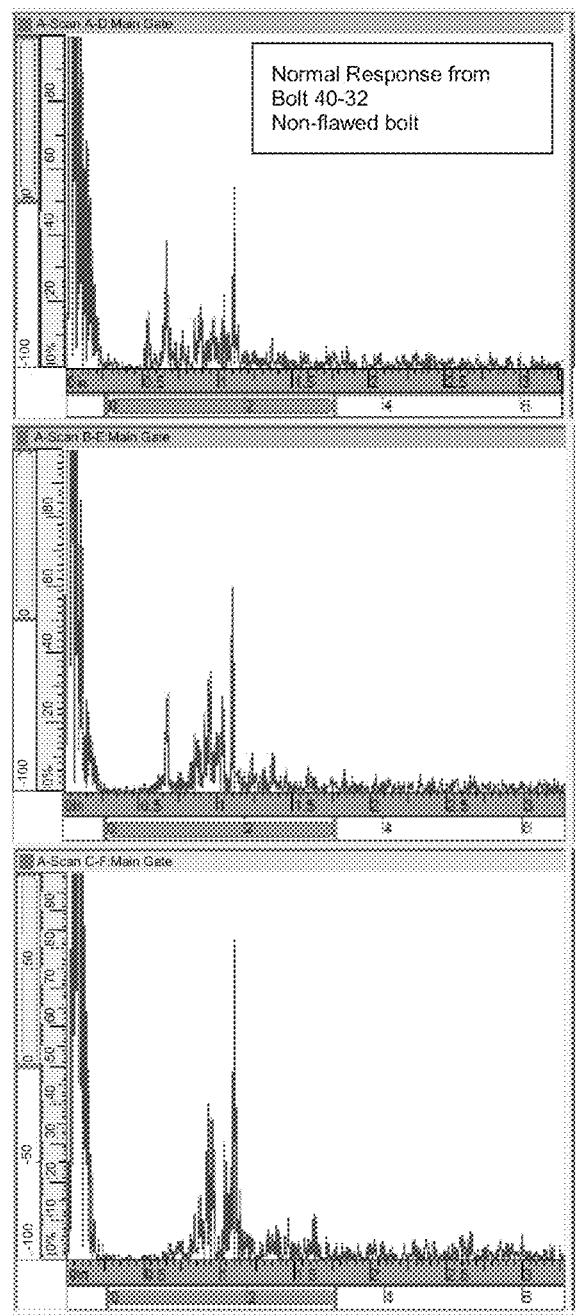
Figure 24:
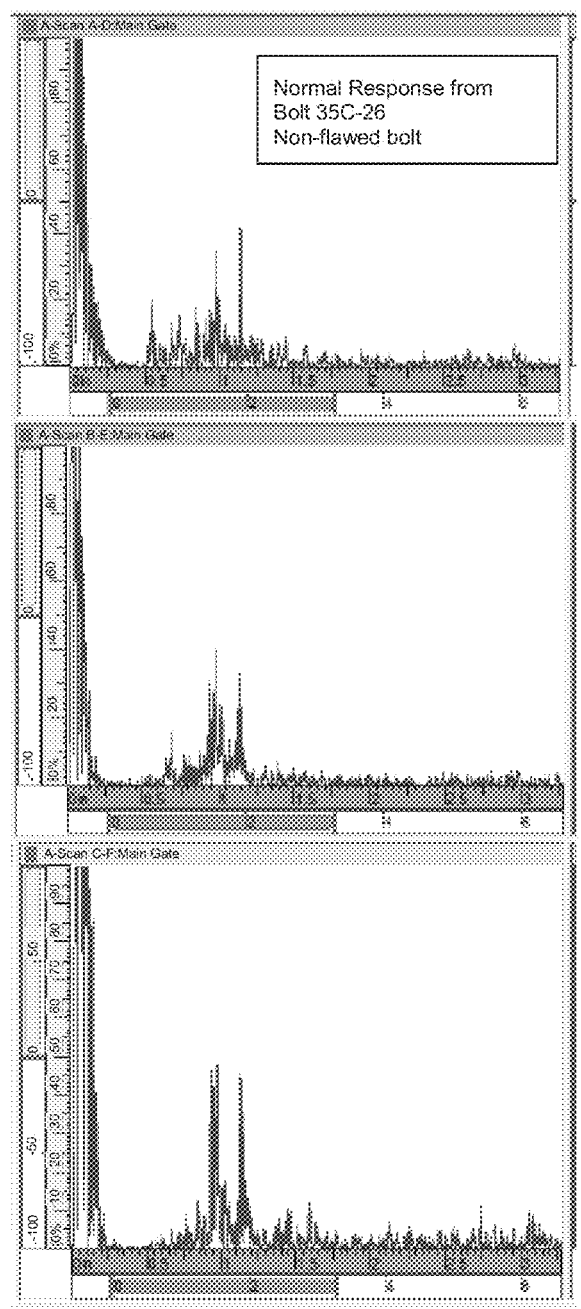

FIGS. 19 and 20 present top views from the bolt head 11 and shows the effect of flaw 28 position relative the flats 13 for detection with the dual-opposite technique. FIG. 19 illustrates an elliptically shaped flaw 28 that is approximately 25% deep and centered between two flats 13. This is the least optimum position for this technique because only a small portion of the flaw 28 is contributing to the reflection of the beam 28 across the bolt 10. Shallow flaws with this orientation may escape detection with this technique because the reflected energy may not be of sufficient strength to distinguish it from a non-flawed area of the bolt. FIG. 20 illustrates the same flaw as FIG. 19, but it is on only one of the flats 13. Shallow flaws with this alignment will likely be detected because the beam is centered on the flaw and provides the maximum reflecting surface.

Deeper flaws are likely to span multiple flats 13 and be detected with multiple dual-opposite channels. In this regard, the number of channels that detect the flaw may be an indicator of the flaw depth; however, flaw size is not relevant to disposition the condition of the bolt. The method used to minimize false calls with this technique involves a second acquisition of the data but with the probe rotated at least 60°. If the indication is relevant and present on only one or two channels, it will move to the channels corresponding to the probe rotation. For example, if the indication was detected on channel BE during the first acquisition and then after rotating the probe 60° the indication appears on channel CF, the indication will be considered relevant and the bolt considered cracked. If the indication does not change channels corresponding to the probe rotation position it will be considered non-relevant.

FIGS. 21-24 each show typical UT responses from flaws with no tilt angles (flat) and 25% flaw depths with the dual-opposite technique. Responses obtained from two non-flawed bolts are also shown for comparison. The images include the displays from each of the three channels used for this technique. As evidenced by the responses, flaws are easily detectable with good signal to noise ratio.

While the preferred embodiments of the present invention have been described above, it should be understood that they have been presented by way of example only, and not of limitation. It will be apparent to persons skilled in the relevant art that various changes in form and detail can be made therein without departing from the spirit and scope of the invention. Thus the present invention should not be limited by the above-described exemplary embodiments, but should be defined only in accordance with the following claims and their equivalents. Furthermore, while certain advantages of the invention have been described herein, it is to be understood that not necessarily all such advantages may be achieved in accordance with any particular embodiment of the invention. Thus, for example, those skilled in the art will recognize that the invention may be embodied or carried out a manner that achieves or optimizes one advantage or group of advantages as taught herein without necessarily achieving other advantages as may be taught or suggested herein.

What is claimed is:

1. An inspection tool, comprising:
a head configured for placement within a socket of a fastener to be inspected, the fastener having a longitudinal axis; and
at least one transducer coupled to said head, said transducer oriented such that when said head is positioned within the socket, said transducer is positioned to impart energy into the fastener at an angle relative to the longitudinal axis, wherein:
the fastener socket has a number of fastener walls that are substantially parallel to the longitudinal axis;
said head is configured to substantially fill an elevation of the socket with a number of head walls equal to the number of fastener walls; and
said at least one transducer includes a plurality of transducers in an amount equal to the number of fastener walls, the transducers being integrally connected to the head and fully removable from the fastener socket, each of the transducers configured for facing one of the fastener walls.

2. The inspection tool of claim 1, wherein:
the fastener walls are each formed by a fastener flat surface;
the head walls are each formed by a head flat surface.

3. The inspection tool of claim 1, wherein said plurality of transducers are arranged such that each of said head walls has one of said plurality of transducers positioned thereon such that when said head is inserted into the fastener socket one of said plurality of transducers is positioned adjacent each of said fastener walls.

4. The inspection tool of claim 1, wherein said transducer is positioned to impart energy at an angle of approximately 35°-55° relative to the longitudinal axis.

5. The inspection tool of claim 1, wherein each of the transducers is configured such that, when placed in the socket, each of the transducers is positioned to impart energy through the respective fastener wall facing the transducer.

6. A method of inspecting a fastener having a body and a head defining a socket, comprising:
providing an inspection tool having a head configured for placement within a socket of a fastener to be inspected, the fastener having a longitudinal axis, and a plurality of transducers arranged in an array such that when said head is positioned within the socket said transducers are substantially evenly spaced adjacent an internal surface of the socket;
positioning said head within the socket;
imparting ultrasonic energy from one or more of said transducers through the fastener head to the fastener body; and
receiving ultrasonic energy through one or more of said transducers, said received ultrasonic energy having traveled and reflected through the fastener body, wherein:
the fastener socket has a number of fastener walls that are substantially parallel to the longitudinal axis;
said head is configured to substantially fill an elevation of the socket with a number of head walls equal to the number of fastener walls; and
said plurality of transducers are in an amount equal to the number of fastener walls, the transducers being integrally connected to the head and fully removable from the fastener socket, each of the transducers configured for facing one of the fastener walls.

7. The method of claim 6, wherein said imparting includes imparting ultrasonic energy through a surface of the fastener head that is substantially parallel to fastener longitudinal axis.

8. The method of claim 6, wherein said imparting includes imparting ultrasonic energy into the fastener at an angle of approximately 35°-55° relative to the longitudinal axis.

9. The method of claim 6, wherein said imparting and receiving is conducted by different ones of said plurality of transducers.

10. The method of claim 9, wherein said one of said plurality of transducers imparting said ultrasonic energy is positioned adjacent said one of said plurality of transducers receiving said ultrasonic energy.

11. The method of claim 9, wherein said one of said plurality of transducers imparting said ultrasonic energy is positioned opposite said one of said plurality of transducers receiving said ultrasonic energy.

12. The method of claim 6, wherein said imparting and receiving is conducted by a single one of said plurality of transducers.

13. A non-destructive inspection tool for inspecting a fastener having a head connected to a shaft and having a longitudinal axis, the fastener head having a socket, comprising:
a probe configured for placement within the socket; and
at least one transducer coupled to said probe, said at least one transducer oriented such that when said probe is positioned within the socket, said transducer is positioned to impart energy into the fastener toward the shaft at an angle relative to the longitudinal axis, wherein:
the fastener socket has a number of fastener walls that are substantially parallel to the longitudinal axis;
said probe is configured to substantially fill an elevation of the socket with a number of probe walls equal to the number of fastener walls; and
said at least one transducer includes a plurality of transducers in an amount equal to the number of fastener walls, the transducers being integrally connected to the head and fully removable from the fastener socket, each of the transducers configured for facing one of the fastener walls.

14. The non-destructive inspection tool of claim 13, wherein said plurality of transducers are arranged such that each of said probe walls has one of said plurality of transducers positioned thereon such that when said probe is inserted into the fastener socket one of said plurality of transducers is positioned adjacent each of said fastener walls.

15. The non-destructive inspection tool of claim 13, wherein:
   the fastener includes a first end and a second end, the socket positioned in the first end; and
   said at least one transducer is positioned to impart energy into the fastener toward the second end of the fastener.

16. The non-destructive inspection tool of claim 15, wherein said at least one transducer is positioned to impart energy into the fastener at an angle of approximately 35°-55° relative to the longitudinal axis.

* * * * *